United States Patent
Otto et al.

[11] Patent Number: 5,908,414
[45] Date of Patent: Jun. 1, 1999

[54] IMPLANTABLE INFUSION PUMP

[75] Inventors: Karl-Heinz Otto; Manfred Wieland, both of Kiel; Hans Baumann, Raisdorf; Jörg-Roger Peters, Bordesholm, all of Germany

[73] Assignee: Tricumed GmbH, Germany

[21] Appl. No.: 08/961,372

[22] Filed: Oct. 30, 1997

Related U.S. Application Data

[63] Continuation of application No. PCT/DE96/00771, May 3, 1996, abandoned.

[30]  Foreign Application Priority Data

May 3, 1995 [DE] Germany .......................... 195 15 722

[51] Int. Cl.$^6$ ...................................................... A61K 9/22
[52] U.S. Cl. ........................................ 604/891.1; 604/141
[58] Field of Search .................................... 604/131, 140, 604/141, 145, 146, 151, 143, 147, 93, 891.1; 128/DIG. 12

[56]  References Cited

U.S. PATENT DOCUMENTS

| | | |
|---|---|---|
| 3,921,916 | 11/1975 | Bassous . |
| 4,537,680 | 8/1985 | Barth . |
| 4,715,852 | 12/1987 | Reinicke et al. .......................... 604/131 |
| 4,793,825 | 12/1988 | Benjamnin et al. ...................... 604/145 |
| 5,176,360 | 1/1993 | Winchell et al. . |

FOREIGN PATENT DOCUMENTS

| | | |
|---|---|---|
| 0 189 940 | 1/1986 | European Pat. Off. . |
| 0 369 712 | 11/1988 | European Pat. Off. . |
| 19515722 | 7/1996 | Germany . |

*Primary Examiner*—Mark Bockelman
*Attorney, Agent, or Firm*—Larson & Larson, P.A.; James E. Larson

[57]  ABSTRACT

An improved implantable infusion pump comprises a propellant chamber, a medicament chamber, and a throttle section. Enclosed within the throttle section is a medicament delivery system comprising a chip having a fluid path etched in an upper surface, inlet and outlet depressions formed in the chip lower and upper surfaces respectively, and a channel formed through the chip connecting the inlet with the fluid path. A planar cover, preferably transparent, covers the chip upper surface. A pair of wafers surround the chip within the throttle section and pair of silicon coatings are positioned between the chip and the pair of wafers. Various bores, apertures, and recesses are formed in the wafers, the cover, and the coatings, for permitting the medicament fluid to pass through the throttle section. An alternate embodiment employs a plurality of fluid paths and a plurality of outlets permitting different throttle resistance.

8 Claims, 1 Drawing Sheet

IMPLANTABLE INFUSION PUMP

This application is a continuation of International Application PCT/DE96/00771 with an International filing date of May 3, 1996, now abandoned.

BACKGROUND OF THE INVENTION

1. Field of Invention

The present invention relates to an implantable infusion pump. More particularly, it relates to an implantable infusion pump employing a chip as a throttle section.

2. Background of the Prior Art

Implantable infusion pumps are known in the prior art and comprise of a housing having a pair of chambers formed therein. A first chamber receives a propellant for generating a vapor pressure, while a second chamber receives a medicament. Also provided is a throttle section for metering the delivery of medicament which is delivered to a catheter opening in the body of a patient, the throttle section formed as a chip with a fluid path etched therein. Such can be seen in European Patent 0 189 940. Unfortunately, such prior art devices have shown not to have a reliable inlet-outlet connection, nor one that is resistant against shock. Such an improved device is needed.

SUMMARY OF THE INVENTION

The construction of the throttle section as a chip and the etching in of the fluid path using a photolithographic process makes it possible to obtain very considerable sections. In the case of a mutual spacing of the fluid paths of 10 pm, it is e.g. mathematically possible to obtain a throttle section length of 100 m/cm². The cross-section of the fluid path can be very accurately chosen through the depth of etching.

Although a construction is possible, in which two mirror symmetrical bodies provided with a fluid path are placed on one another, preference is given to an embodiment, in which a highly planar cover is bonded onto the upper surface of the chip and is supported on the zones between the fluid paths. This cover should be made from a transparent glass, which permits a visual checking of the migration of the medicament through the throttle section prior to the fitting of the chip in the infusion pump.

In a preferred embodiment the inlet and outlet are constructed as depressions etched into the surface and the depression forming the inlet is provided with a channel leading to the back face of the chip. At least the upper surface or the lower surface of the chip can be provided with a metal wafer, which is provided with bores aligned with the inlet or outlet. It is recommended to have between the surface of the chip and the metal wafer a coating of silicone (or a corresponding elastic material), provided with a recess aligned with the inlet or outlet.

In a preferred embodiment, on the chip are formed a plurality of fluid paths representing a different throttle resistance, the inlet being centrally constructed and the outlets of the individual fluid paths are arranged symmetrically to the inlet point. This makes it possible to choose for the infusion pump the particular throttle resistance as a function of the installation position of the chip.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE PREFERRED EMBODIMENT

Figure 1:
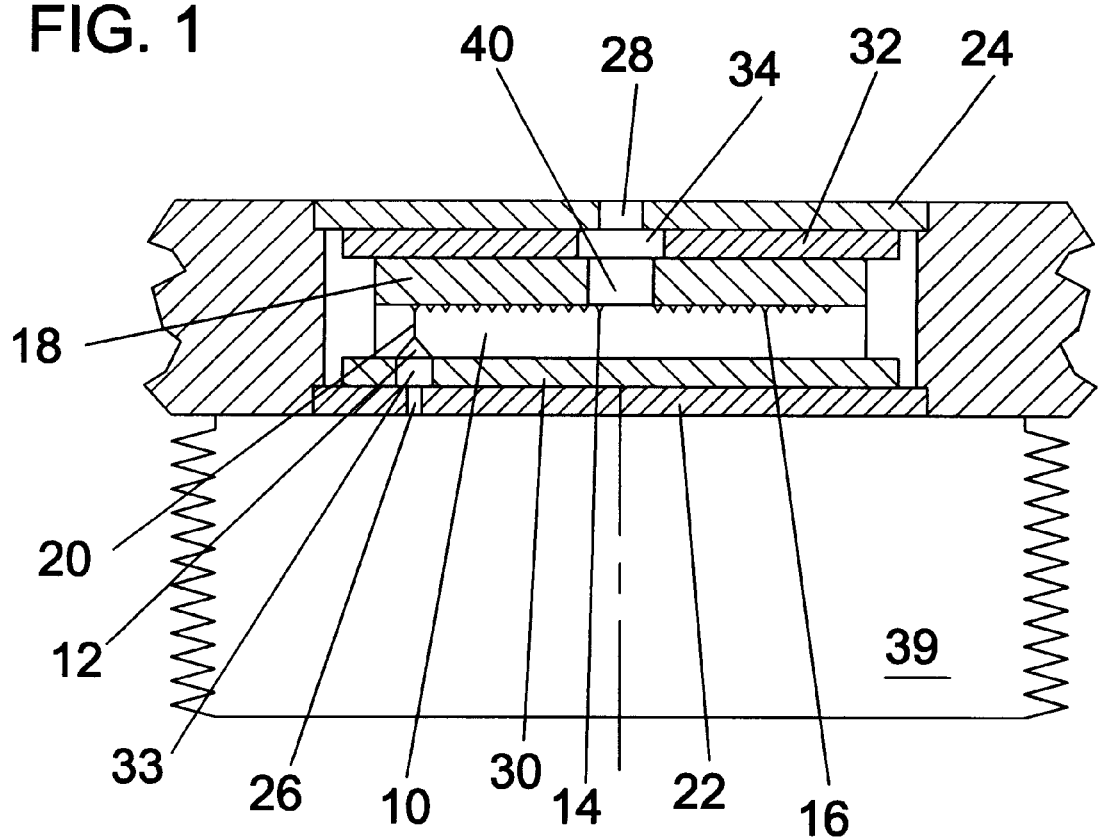
FIG. 1 A sectional view of a chip inserted in an only partly shown infusion pump.

FIG. 1 shows in cross-sectional form part of the infusion pump. It can be seen that the upper portion of the medicament chamber 39 is provided with a recess, in which is placed a chip 10. The upper surface of the chip 10 is provided with a plurality of meandering fluid paths 16 linking an inlet 12 with an outlet 14. These fluid paths 16 are etched in the upper surface of the chip 10 by a photolithographic process, such as is known for the manufacture of semiconductor circuits. A cover 18 made from transparent glass is placed on the upper surface of the chip 10 and in this way upwardly bounds the fluid paths 16.

The chip 10 is downwardly provided with a first silicon coating 30, a second silicon coating 32 being located on the cover 18. This construction of chip 10, cover 18 and silicon coatings 30, 32 is surrounded at the top and bottom by metal wafers 22, 24, by means of which the arrangement is fixed, preferably laser welded, in the upper cover of the medicament chamber 39. The silicone coatings 30, 32 serve to absorb shocks, so as to protect the chip 10 and cover 18 against mechanical shocks.

The lower, metal wafer 22 is provided with a bore 26 and the silicon coating 30 with a recess 33. The bore 26 and recess 33 are aligned with an inlet 12 of the chip 10, which leads by means of a channel 20 passed through the chip to the fluid path 16 in the upper surface of the chip 10.

The cover 18 has a central bore 40, which is aligned with a centrally positioned outlet 14 of the fluid path 16. The upper silicon coating 32 is provided with a recess 34 and the upper, metal wafer 24 with a bore 28, also aligned with the outlet 14 of the fluid path.

The medicament received by the medicament chamber 39 can in this way pass through the channel 20 and fluid path 16 upwards through the bore 28 in the upper, metal wafer 24, on which is provided a not shown connection to a catheter.

Figure 2:
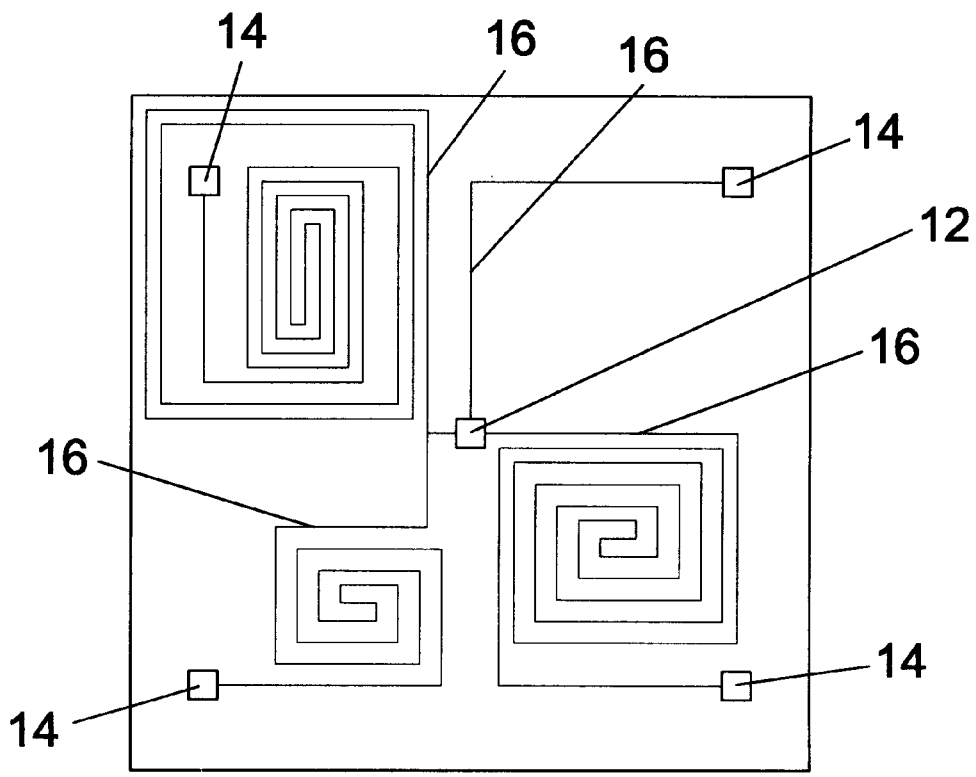
FIG. 2 A plan view of the upper surface of the chip.

FIG. 2 shows that with a square construction of the chip 10, the inlet 12 centrally positioned, whilst the four outlets 14 are located adjacent to the four corners of the chip equidistantly with respect to the particular corner. Through a suitable fitting, this makes it possible to choose which of the four throttle sections is active. In this way, the throttle resistance can be chosen in accordance with the particular requirements.

Having thus described the invention, what is claimed and desired to be secured by Letters Patent is:

1. An implantable infusion pump having a housing, a propellant chamber, a medicament chamber, and a throttle section, the implantable infusion pump communicating with a catheter opening in a body of a patient, the improvement comprising:
   (a) a chip having an upper and lower surface positioned within the throttle section, the chip upper surface having at least one fluid path formed therein,
   (b) a planar cover having an aperture formed therein, the cover positioned on the chip upper surface,
   (c) an inlet depression formed on the chip lower surface,
   (d) at least one outlet depression formed on the chip upper surface communicating with the at least one fluid path,
   (e) a channel formed through the chip such that the inlet depression communicates with the at least one fluid path, (f) an upper wafer positioned above the chip upper surface, the upper wafer having a first bore formed therein such that the first bore axially aligns with the cover aperture and communicates with one of the at least one outlet depressions, and (g) a lower wafer positioned below the chip lower surface, the lower wafer having a second bore formed therein such that the second bore axially aligns with the inlet depression.

2. The implantable infusion pump of claim 1, further comprising:

(a) an upper coating positioned between the upper wafer and the planar cover, the upper coating having a first recess formed therein such that the first recess axially aligns with the cover aperture and the upper wafer bore and communicates with one of the at least one outlet depressions, and (b) a lower coating positioned between the lower wafer and the chip lower surface, the lower coating having a second recess formed therein such that the second recess axially aligns with the lower wafer bore and the inlet depression.

3. The implantable infusion pump of claim 2, wherein silicon coatings are employed.

4. The implantable infusion pump of claim 1, wherein a plurlaity of fluid paths are employed.

5. The implantable infusion pump of claim 4, wherein a plurality of outlet depressions are employed.

6. The implantable infusion pump of claim 5, wherein four outlet depressions are employed and are positioned in respective four corners of the chip such that each outlet is of a equal distance from the inlet.

7. The implantable infusion pump of claim 1, wherein a plurality of outlet depressions are employed.

8. The implantable infusion pump of claim 7, wherein four outlet depressions are employed and are positioned in respective four corners of the chip such that each outlet is of a equal distance from the inlet.

* * * * *